United States Patent [19]

Wholey et al.

[11] Patent Number: 4,723,549
[45] Date of Patent: Feb. 9, 1988

[54] METHOD AND APPARATUS FOR DILATING BLOOD VESSELS

[76] Inventors: Mark H. Wholey, 816 Woodland Ave., Pittsburgh, Pa. 15139; Mark L. Nagurka, 5370 Melvin St., Pittsburgh, Pa. 15217; Robert S. Katz, 33 Dinsmore Ave., Apt. 104, Framingham, Mass. 01701

[21] Appl. No.: 908,988

[22] Filed: Sep. 18, 1986

[51] Int. Cl.⁴ ............................................. A61M 25/00
[52] U.S. Cl. .................... 128/344; 128/325; 604/101
[58] Field of Search ................ 604/101, 105; 128/341–345, 348.1, 328, 325

[56] References Cited

U.S. PATENT DOCUMENTS

| | | |
|---|---|---|
| 2,854,983 | 10/1958 | Baskin .............................. 604/105 X |
| 3,540,431 | 11/1970 | Mohm-Uddlm . |
| 3,692,029 | 9/1972 | Adair ..................... 604/105 |
| 3,952,747 | 4/1976 | Kimmell, Jr. . |
| 4,295,464 | 10/1981 | Shihata . |
| 4,299,226 | 11/1981 | Banka . |
| 4,404,971 | 9/1983 | LeVeen . |
| 4,423,725 | 1/1984 | Baran et al. . |
| 4,425,908 | 1/1984 | Simon . |
| 4,445,892 | 5/1984 | Hussein . |
| 4,493,711 | 1/1985 | Chin et al. . |
| 4,512,762 | 4/1985 | Spears . |
| 4,564,014 | 1/1986 | Fogarty et al. . |
| 4,573,966 | 3/1986 | Weikle et al. . |
| 4,585,000 | 4/1986 | Hershenson .................. 128/345 |
| 4,610,662 | 9/1986 | Weckl et al. ................. 604/101 X |

FOREIGN PATENT DOCUMENTS 3107392 9/1982 Fed. Rep. of Germany ...... 128/344

Primary Examiner—Dalton L. Truluck
Attorney, Agent, or Firm—Richard V. Westerhoff; Arnold B. Silverman

[57] ABSTRACT

A catheter for dilating occluded or stenotic blood vessels includes a collapsible filter device disposed between a dilating balloon and the distal end of the catheter. The collapsible filter device comprises a plurality of resilient ribs secured to the catheter at or adjacent the distal end thereof and extending generally axially toward the dilating balloon. Inflation of a filter balloon extends the ribs outward against the vessel wall to stretch filter material secured to the ribs across the vessel to form a cup shaped trap for fragments of a stenosis loosened by the dilating balloon. Upon deflation of the filter balloon, the resilient ribs retract against the catheter to retain the trapped fragments during withdrawal of the catheter. In the preferred embodiment, the ends of the ribs projecting generally toward the dilating balloon are secured to a ring which slides along the catheter. In use, the filter is extended and then the dilating balloon is inflated. Blood flow established by deflation of the dilating balloon carries stenosis fragments into the filter.

10 Claims, 6 Drawing Figures

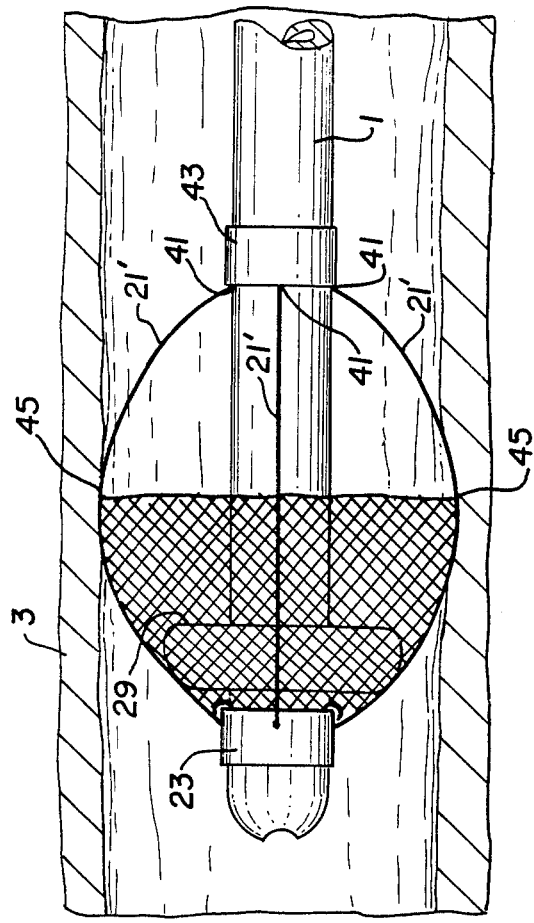
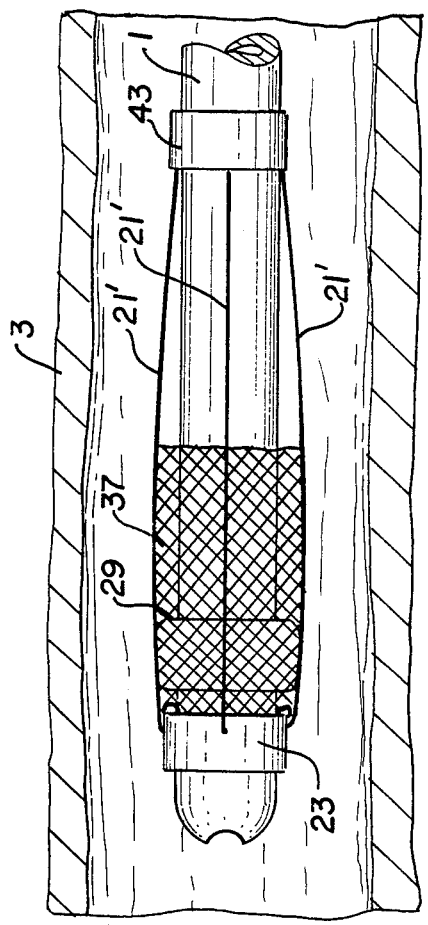
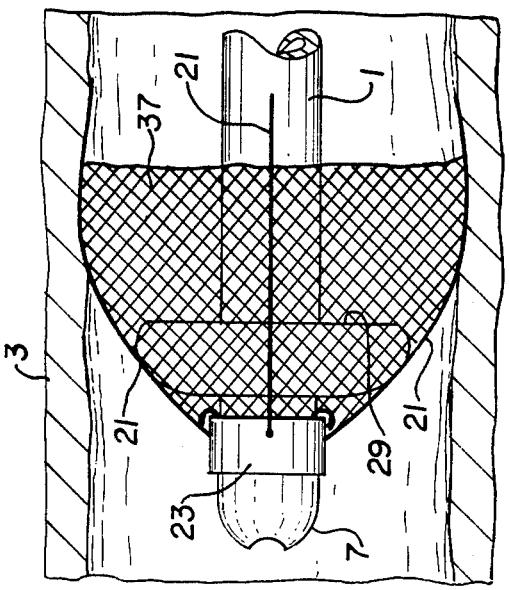
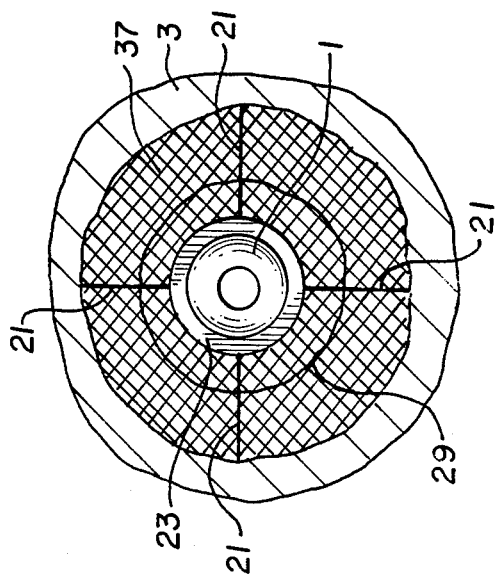

METHOD AND APPARATUS FOR DILATING BLOOD VESSELS

BACKGROUND OF THE INVENTION

1. Field of the Invention

This invention relates to an apparatus and method for dilating occluded or stenotic blood vessels and more particularly to such an apparatus and method which include inflating a dilating balloon carried by a catheter to widen a passage through a stenosis, and trapping fragments of plaque broken off by dilation in a filter which collapses in a manner which retains the fragments while the catheter is removed from the blood vessel.

2. Background Information

It is becoming common practice today to open occluded (i.e. blocked) or stenotic (i.e. narrowed) blood vessels by inserting a catheter carrying a toroidal balloon into the vessel and inflating the balloon to press the stenosis radially outward against the wall of the blood vessel. While this is often effective in increasing blood flow through the vessel, embolic fragments of the stenosis can break loose and be carried by the flow to other parts of the circulatory system where they can lodge and cause a blockage. It is also important in such a procedure that the interruption of blood flow through the vessel be minimized. This is especially important in thecase of the carotid artery carrying blood to the brain of a human.

It is a primary purpose of the present invention to provide a catheter for dilating an occluded or stenotic blood vessel which includes, in addition to a dilating balloon, a filter device for trapping embolic fragments of the stenosis dislodged by dilation.

It is another important object of the invention to provide such a filter device carried by the catheter which is insertable into the occluded or stenotic vessel in a retracted position, and can be easily and reliably remotely extended.

It is yet another object of the invention to provide such a catheter with a filter which securely retains embolic fragments of the stenosis when the filter is retracted for removal from the blood vessel.

It is still another object of the invention to provide such a catheter with an extendable and retractable filter which minimizes trauma as the catheter is inserted and withdrawn from the blood vessel.

It is also an important object of the invention to provide a method of dilating occluded or stenotic blood vessels which includes mechanically trappng embolic fragments of the stenosis dislodged by dilation and removing them from the vessel without spillage.

It is a further object of the invention to achieve the previous objects with minimum interruption of blood flow through the vessel.

SUMMARY OF THE INVENTION

These and other objects are realized by the invention which includes a flexible catheter with a dilating balloon, and a collapsible filter device attached to the catheter between the dilating balloon and the distal end of the catheter. The filter device is extendable outward toward the interior wall of the blood vessel to trap fragments of the stenosis broken loose by the dilating balloon, and retractable along the catheter toward the dilating balloon to retain the trapped fragments while the catheter is withdrawn from the blood vessel.

In the exemplary embodiments, the filter includes a plurality of ribs angularly spaced around the catheter, and, in a closed position, extending generally axially toward the dilating balloon. Filter material bridges the gaps between the ribs to form a cup shaped trap. Means for urging the ends of the ribs extending toward the dilating balloon outward against the wall of he blood vessel preferably comprise a filter balloon inflated through a lumen extending along the catheter. The filter balloon is placed adjacent the pivoted ends of ribs toward the distal end of the catheter such that even when inflated sufficiently to fully extend the ribs it does not block flow through the blood vessel.

In the preferred form of the invention, the ends of the ribs extending toward the dilating balloon are secured to a ring slidable along the catheter as the mid portions of the ribs bow outward with inflation of the filter balloon. With this arrangement, the proximal ends of the ribs are restrained to slide along the outside wall of the catheter thereby minimizing the likelihood of these ends of the ribs becoming snagged.

The invention also embraces the method of dilating an occluded or stenotic blood vessel by inserting a catheter in the vessel with the dilating balloon aligned with the stenosis. A collapsible filter mounted on the catheter downstream of the stenosis is expanded first to filter fluid in the blood vessel. The dilating balloon is then inflated to press the stenosis radially outward and fracture the stenosis. The dilating balloon is deflated and reestablished blood flow carries any fragments of the stenosis into the filter. Retraction of the filter radially inward and axially toward the dilating balloon retains the trapped fragments while the catheter is withdrawn from the vessel.

BRIEF DESCRIPTION OF THE DRAWINGS

A full understanding of the invention can be gained from the following description when read in conjunction with the accompanying drawings in which:

FIG. 2 is a partial side elevation view of the catheter of FIG. 1 showing the filter in the extended position;

FIG. 3 is an end elevation view of the extended filter of FIG. 2;

FIG. 5 is a partial side elevation view of a modified, preferred form of the filter shown in the extended position; and FIG. 6 is a partial side elevation view of the filter of FIG. 5 shown in the retracted position.

DESCRIPTION OF THE PREFERRED EMBODIMENTS

Figure 1:
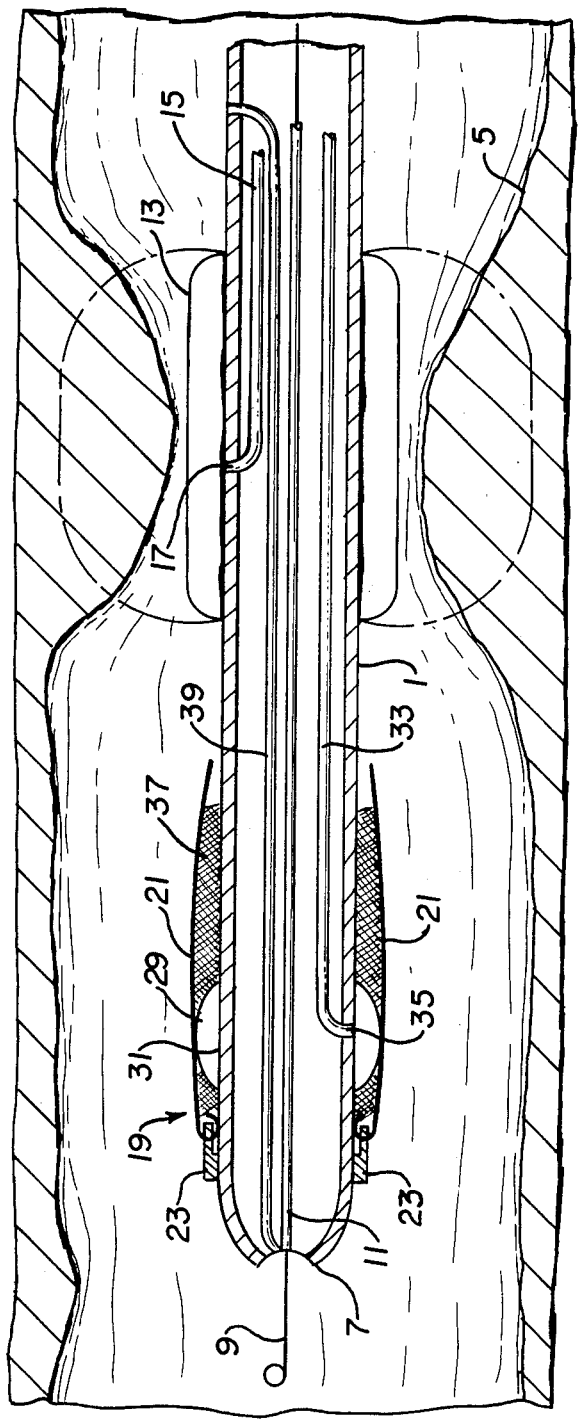
FIG. 1 is a longitudinal section through a first embodiment of a filter equipped dilating catheter in accordance with the teachings of the invention in place adjacent a stenosis in a blood vessel with the dilating balloon deflated and the filter retracted.

As shown in FIGS. 1–3, the device of the invention includes a flexible elongated catheter 1 which is inserted into a blood vessel 3 narrowed by a stenosis 5 through an incision (not shown) upstream of the stenosis 5. The catheter 1 is guided into place with the distal end 7 downstream of the stenosis 5 by a guide wire 9 which passes through a guide lumen 11 in the catheter. Radiography may be used as is known to aid in positioning the catheter. A toroidal dilating balloon 13 is secured to the catheter 1 by known techniques at a location spaced from the distal end 7 of the catheter. A dilating balloon lumen 15 in the catheter supplies pressurizing fluid to the dilating balloon through an orifice 17.

Figure 4:
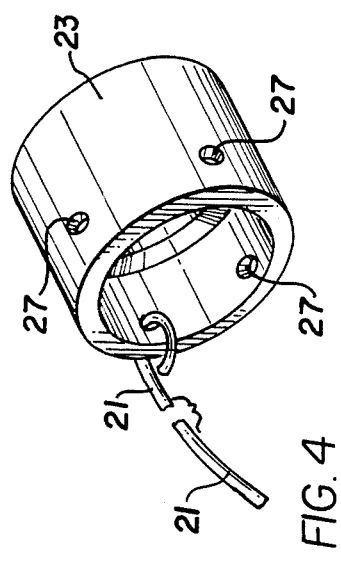
FIG. 4 is an enlarged isometric view of a ring which pivotally mounts the ribs of the filter of FIGS. 1 through 3 to a catheter.

A filter device 19 is affixed to the catheter between the distal end 7 and the dilating balloon 13. This filter device includes a plurality of ribs 21, of which four are shown in the embodiments illustrated, equiangularly spaced around the catheter 1. A device with six equiangularly spaced ribs 21 has also been constructed. The ribs 21 are pivotally secured to the catheter at one end and extend gradually axially along the catheter in the stowed position shown in FIG. 1. The ribs 21 are formed of a resilient material, preferably stainless steel or a suitable plastic. In the exemplary embodiment, the ribs 21 are 0.006 inch diameter steel wires. These wires are pivotally mounted on the catheter by a ring 23 which in turn is secured to the catheter, such as by an adhesive 25. The ring 23, which is shown enlarged in FIG. 4, is counterbored 23' at the end toward the dilating balloon 13 and is provided with radial apertures 27 through which the wire ribs 23 are hooked. The resilient ribs 21 are prestressed or preformed such that they are biased inward against the catheter.

A toroidal filter balloon 29 is secured to the catheter 1, such as by an adhesive 31 or by other known techniques, under the ribs 21 adjacent the ring 23. Pressurizing fluid is supplied to the filter balloon 29 by a filter balloon lumen 33 through orifice 35. Filter material 37 spans the gaps between and is secured to the ribs 21. The filter material 37 is of a mesh fine enough to trap any fragments of the stenosis which might be broken loose yet course enough to permit blood to pass through. In the exemplary embodiment, mesh polyester filter fabric is used. A sufficient number of ribs 23 must be provided to stretch the filter fabric 37 across the vessel.

Inflation of the filter balloon 29 extends the filter by pivoting the ribs 21 until they come into contact with the interior wall of the blood vessel 3 as shown in FIG. 2. The annular filter balloon 29 is of a diameter such that it does not block the blood vessel even when inflated, but being positioned close to the point at which the ribs are secured to the catheter, it is effective to fully extend the ribs 21. With the ribs 21 extended into contact with the wall of the blood vessel the filter material is stretched across the blood vessel to form a cup shaped opening toward the dilating balloon to catch any fragments broken loose from the stenosis 5. The resiliency or compliance of the ribs 21 causes them to retract to the stowed position shown in FIG. 1 when the filter balloon 29 is deflated. As they collapse in umbrella fashion toward the dilating balloon 13, any fragments of the stenosis 5 are retained in a deep pocket formed in the filter material 37 where they remain as the catheter 1 is withdrawn from the blood vessel.

If desired, a bypass lumen 39 can be provided in the catheter extending from a point proximal to the dilating balloon 13 to the distal end 7. This bypass assures blood flow through the vessel even for the short periods of time when the dilating balloon is inflated. Alternatively, the bypass lumen 39 need only bypass the dilating balloon 13 so that the bypassed blood passes through the filter device 21.

In the preferred form of the filter shown in FIGS. 5 and 6, the ends 41 of the resilient ribs 21' which extend toward the dilating balloon 13 are secured to a second ring 43 which is slidable along the catheter 1. In the exemplary embodiment, the wire ribs 21' are cantilevered from the ring 43, however, they can also be pivotally mounted to the ring 43 as they are to the ring 23. Inflation of the filter balloon 29 causes the ribs 21' to bow outward as shown in FIG. 5 until points, 45, in their mid portion contact the wall of the blood vessel. In this configuration, the filter material 37 only covers the ribs 21' from their distal ends to about the point 45 of contact with the wall of the blood vessel to form the cup shaped trap. Upon deflation of the filter balloon 29, the resiliency or compliance of the ribs 21' returns then to the stowed position shown in FIG. 6 and the ring 41 slides along the catheter in the direction of the dilating balloon. An advantage of this embodiment is that there are no protruding ends of the ribs, thereby minimizing any possibility of the ribs snagging on the blood vessel as the catheter 1 is withdrawn.

In use, the catheter 1 is inserted with the aid of guide wire 9 and radiography into the occluded or stenotic blood vessel 3 with the deflated dilating balloon 13 aligned with the stenosis 5 and the retracted filter device 21 downstream of the stenosis as shown in FIG. 1. Pressurizing fluid, preferably in the form of a saline solution, is injected into the lumen 33 to inflate the filter balloon 29 which extends the ribs 21 or 21' outward against the wall of the blood vessel 3 forming a cup shaped trap with the filter material 37 as shown in FIGS. 2 and 5. In the case of the preferred embodiment of FIG. 5, this causes the ring 41 to slide toward the distal end of the catheter 1. Although blood flow may be partially interrupted by extension of the filter, the mesh of the filter material is coarse enough such that the blood constituents but not embolic fragmentation can pass through.

With the filter device 21 extended, pressurizing fluid, preferably a saline solution, is injected into lumen 17 to inflate the dilating balloon 13 to the position shown by the chain line in FIG. 1 thereby pressing the plaque forming the stenosis 5 radially outward against the wall of the blood vessel 3. This results in fragmentation of at least portions of the stenosis. Inflation of the dilating balloon interrupts the flow of blood unless a bypass lumen 39 is provided; however, this is a temporary interruption lasting only a matter of seconds.

Deflation of the dilating balloon restores blood flow which carries any fragments of the stenosis broken off by dilation downstream into the cup shaped trap formed by outstretched filter material 37. After waiting sufficient time to assure that all loose fragments have been carried into the filter, the filter balloon 29 is deflated causing the ribs 23 or 23' to return to the stowed position. In the case of the preferred embodiment, this causes the ring 41 to slide toward the dilating balloon 13. As the ribs retract, the filter material 37 forms an elongated pocket which retains the dislodged fragments of the stenosis during withdrawal of the catheter from the blood vessel.

The present invention interrupts blood flow for only a short duration while the dilating balloon is inflated. It also provides a positive, reliable mechanical filter to assure that fragments are collected and removed from the vessel.

The invention is suitable for use in dilating occluded or stenotic blood vessels in humans and animals. For occluded arteries, there could be some initial untrapped fragmentation as the catheter 1 with the retracted filter 19 is pushed through the occlusion. Subsequently, the catheter may be used to significantly open the artery with any resulting fragmentation being caught by the filter 19.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. Apparatus for dilating occluded and stenotic blood vessels comprising:

an elongated flexible catheter the distal end of which is insertable into said blood vessel;

a dilating balloon affixed to the catheter at a location spaced from the distal end of the catheter;

means for selectively introducing a pressurized fluid into the dilating balloon to inflate it against a stenosis and thereby dilate the vessel; and for withdrawing said fluid to deflate the dilating balloon;

a collapsible filter device attached to the catheter between the dilating balloon and the distal end of the catheter which filter is extendable outward against the wall of the blood vessel to trap fragments of the stenosis broken by inflation of the dilating balloon while allowing passage of blood therethrough, and retractable along the catheter to retain the trapped fragments of the stenosis while the catheter is withdrawn from the blood vessel, said filter device comprising a plurality of ribs resiliently biased inward along the catheter angularly spaced around the catheter and extending generally axially along the catheter in the direction of the dilating balloon, and filter material bridging said ribs; and means for extending and retracting the filter device to selectively urge said ribs outward against the walls of the blood vessel to spread the filter material across the blood vessel, said means comprising a filter balloon disposed between the catheter and said resilient ribs, and a filter balloon lumen in said catheter through which fluid is selectively supplied to inflate the filter balloon and thereby extend said filter and through which fluid is withdrawn to deflate the filter balloon and thereby retract the filter, the diameter of said filter balloon when inflated being less than the diameter of the blood vessel.

2. The apparatus of claim 1 wherein the ends of the resilient ribs extending toward the dilating balloon are secured to a ring slidable along the catheter as the ribs are extended and retracted by inflation and deflation of the filter balloon, said filter material only bridging said ribs between the distal ends of the ribs and about a midportion of the ribs which bears against the vessel wall.

3. Apparatus for dilating occluded and stenotic blood vessels comprising;

an elongated flexible catheter the distal end of which is insertable in the blood vessel to be dilated;

a dilating balloon affixed to the catheter at a location spaced from said distal end;

a first lumen extending along the catheter to the dilating balloon for supplying a fluid to inflate said dilating balloon;

a plurality of resilient ribs angularly spaced around and secured at one end to the catheter adjacent the distal end thereof, said resilient ribs being pivotable from a stowed position wherein they extend generally axially along the catheter toward the dilating balloon and an extended position wherein they pivot outward against the walls of the blood vessel;

a filter fabric spanning the ribs to trap fragments of a stenosis broken loose by the dilating balloon while permitting the passage of blood therethrough when said ribs are extended, and to retain said fragments of the stenosis as the ribs return to the stowed position;

a filter balloon disposed between the ribs and the catheter; and a second lumen extending along the catheter to the filter balloon for selectively supplying a fluid to the filter balloon to inflate the balloon and pivot the ribs outward into contact with the blood vessel wall, said filter balloon even when inflated being smaller in diameter than the extended ribs.

4. The apparatus of claim 3 wherein said resilient ribs are each secured at an end extending toward the dilating balloon to a ring slidable along the catheter as said ribs pivot between the stowed position and the extended position, wherein said filter balloon is disposed adjacent said one end of the ribs to cause said resilient ribs to bow outward between the ends into contact with the wall of the blood vessel, and wherein said filter material spans said ribs between the one end and about where the bowed ribs contact the wall of the blood vessel.

5. The apparatus of claim 3 includiing a bypass lumen in said catheter for bypassing blood flow past the dilating balloon.

6. The apparatus of claim 5 wherein said bypass lumen extends from a point in the catheter on the proximal side of said dilating balloon to the distal end of the catheter.

7. A filter device to be mounted on a balloon catheter downstream of a dilating balloon to trap fragments of a stenosis dislodged by dilation, comprising:

a plurality of resilient ribs angularly spaced around the catheter and formed to extend along the catheter toward the dilating balloon in a stowed position;

means for securing the ends of the ribs remote from the dilating balloon in a stowed position;

a toroidal filter balloon mounted on the catheter adjacent the secured ends of the ribs and radially between the catheter and the ribs;

means for supplying fluid to said filter balloon to inflate the balloon and pivot the ribs radially outward to an extended position in contact with the wall of the blood vessel; said filter balloon even when inflated being smaller in diameter than the extended ribs; and filter material spanning said ribs to form a cup shaped trap for fragments of the stenosis.

8. The filter device of claim 7 including a ring secured to the ends of said ribs toward the dilating ballon, said ring being slidable along the catheter as the ribs are extended and retracted by inflation and deflation of the filter balloon.

9. A method of dilating occluded and stenotic blood vessels:

inserting a catheter into the blood vessel to align adjacent a stenosis in the blood vessel a dilating balloon carried by the catheter;

expanding a collapsible filter carried by the catheter distal to the dilating balloon to filter fluid in the blood vessel passing therethrough;

inflating the dilating balloon to dilate the blood vessel by pressing radially outward on the stenosis;

deflating the dilating balloon and trapping in the filter fragments of the stenosis broken loose by dilation as blood flows through the dilated blood vessel;

retracting the filter radially inward to retain the trapped fragments of the stenosis; and withdrawing the catheter from the blood vessel and with it the fragments of the stenosis.

10. The method of 9 including providing a filter having a plurality of resilient ribs angularly spaced around the catheter and biased generally axially therealong toward the dilating balloon with filter material bridging the ribs and with a filter balloon disposed between the resilient ribs and said catheter and wherein said step of extending the filter comprises injecting fluid into the filter balloon to press the resilient ribs outward against the walls of the blood vessel and wherein the step of retracting the filter comprises withdrawing fluid from the filter balloon so that the resilient ribs retract against the catheter to retain the fragments of the stenosis.

* * * * *

UNITED STATES PATENT AND TRADEMARK OFFICE
CERTIFICATE OF CORRECTION

PATENT NO. : 4,723,549

DATED : February 9, 1988

INVENTOR(S) : MARK H. WHOLEY, MARK L. NAGUARKA and ROBERT S. KATZ

It is certified that error appears in the above-identified patent and that said Letters Patent is hereby corrected as shown below:

Title Page, column 1 under "Inventors", line 3, "5370 Melvin St." should be --5730 Melvin St.--.

Column 1, line 30, "thecase" should read --the case--.

Column 1, line 53, "trappng" should be --trapping--.

Column 2, line 9, "he" should be --the--.

Column 3, line 14, "gradually" should be --generally--.

Column 3, line 35, "course" should be --coarse--.

Claim 5, column 6, line 35, "includiing" should be --including--.

Signed and Sealed this

Twenty-third Day of August, 1988

Attest:

DONALD J. QUIGG

Attesting Officer

Commissioner of Patents and Trademarks